United States Patent [19]

Donadello

[11] Patent Number: 5,312,973
[45] Date of Patent: May 17, 1994

[54] PROCESS FOR PRODUCING N-PHOSPHONO-METHYL-IMINO-DIACETIC ACID

[75] Inventor: Graziello Donadello, Valdagno, Italy

[73] Assignee: Finchimica S.P.A., Manerbio, Italy

[21] Appl. No.: 37,128

[22] Filed: Mar. 25, 1993

[51] Int. Cl.$^5$ ............................................... C07F 9/38
[52] U.S. Cl. ........................................ 562/17; 562/14; 562/554; 562/571
[58] Field of Search .................... 562/8, 14, 17, 554, 562/571

[56] References Cited

U.S. PATENT DOCUMENTS

| | | | |
|---|---|---|---|
| 3,288,846 | 11/1966 | Irani et al. | 260/500 |
| 3,455,675 | 7/1969 | Irani | 71/86 |
| 3,959,361 | 5/1976 | Krueger et al. | 562/17 X |
| 3,969,398 | 7/1976 | Hershman et al. | 562/17 |
| 4,477,390 | 10/1984 | Ledent et al. | 562/14 |
| 4,486,359 | 12/1984 | Hajnóczki et al. | 562/17 |
| 4,548,757 | 10/1985 | Wevers et al. | 562/14 |
| 4,615,840 | 10/1986 | Ledent et al. | 562/14 |
| 4,728,460 | 3/1988 | Ledent et al. | 562/14 |
| 4,931,585 | 6/1990 | Pelyva et al. | 562/17 |

FOREIGN PATENT DOCUMENTS

| | | |
|---|---|---|
| 0155926 | 9/1985 | European Pat. Off. . |
| 2626884 | 8/1989 | France . |
| 1118553 | 3/1986 | Italy . |
| 1575469 | 9/1980 | United Kingdom . |

*Primary Examiner*—Arthur C. Prescott
*Attorney, Agent, or Firm*—Rothwell, Figg, Ernst & Kurz

[57] ABSTRACT

Process for preparing N-phosphono-methyl-iminodiacetic acid by means of phosphonomethylation of iminodiacetic acid performed by reacting an aqueous solution of phosphoric acid and hydrochloric acid, obtained by hydrolysis of phosphorous trichloride, with iminodiacetic acid and formaldehyde, in which phosphorous trichloride is hydrolysed in step (a) with water or an aqueous solution or hydrochloric acid, the reaction temperature and amount of water are regulated such that an aqueous solution of hydrochloric acid and phosphoric acid in a molar ratio of 0.5:1 to 2:1 is formed, and gaseous hydrochloric acid is caused to develop from the reaction medium. The phosphonomethylation reaction is performed in the solution obtained in step (a) in the presence of iminodiacetic acid in a molar ratio of iminodiacetic acid to phosphoric acid between 1:1 and 1:1.2 with the addition of formaldehyde. The N-phosphono-methyl-iminodiacetic acid is then recovered from the reaction medium.

7 Claims, 2 Drawing Sheets

PROCESS FOR PRODUCING N-PHOSPHONO-METHYL-IMINO-DIACETIC ACID

FIELD OF THE INVENTION

The present invention relates to an improved process for preparing N-phosophono-methyl-iminodiacetic acid (PMIDA), also known as N,N-diacetic iminomethylene phosphonic acid.

As is known, a compound of this type is an important intermediate in the preparation of N-phosphonomethyl glycine, a broad spectrum herbicide.

More particularly, the invention relates to a process for preparing PMIDA by means of phosphonomethylation of iminodiacetic acid (IDA) wherein an aqueous solution of phosphoric acid and a strong mineral acid, in particular hydrochloric acid, is reacted with iminodiacetic acid and formaldehyde.

BACKGROUND OF THE INVENTION

U.S. Pat. Nos. 3,288,846 and 3,455,675 describe a process of phosphonomethylation of IDA performed by preparing IDA hydrochloride to which there are added further hydrochloric acid and phosphoric acid, followed by formaldehyde.

Italian Patent No. IT-1 118 553 describes an alternative process in which phosphorous trichloride is used as the phosphorous source. The phosphorous trichloride is hydrolysed in water to produce a solution wherein the reaction products, phosphoric acid and hydrochloric acid, are present in a stoichiometric molar ratio of the hydrolysis reaction of 1:3. The solution obtained in this way is then reacted with iminodiacetic acid and then formaldehyde.

Although phosphorous trichloride is an economical source of phosphorous, it has been established that the hydrolysis in water of phosphorous trichloride, which is an extremely exothermic reaction, is difficult to control and easily leads to byproducts, particularly to oxidation products of the phosphoric acid.

Furthermore, the large amount of hydrochloric acid present in the phosphonomethylation product renders the recovery of PMIDA complicated and expensive, requires a high consumption of energy, does not enable commercial hydrochloric acid to be recovered by distillation since the latter is highly contaminated by formaldehyde, and produces a considerable quantity of liquid refluents which are very expensive to process.

The object of the present invention is to provide an improved process which is easier and more economical, as compared to known processes.

SUMMARY OF THE INVENTION

This and other objects are achieved in a process for preparing N-phosphono-methyl-imini-diacetic acid comprising the steps of:

(a) hydrolysing phosphorous trichloride with water or an aqueous solution of hydrochloric acid, wherein the reaction temperature and amount of water are regulated such that an aqueous solution of hydrochloric acid and phosphoric acid in a molar ratio of 0.5:1 to 2:1 is formed, and gaseous hydrochloric acid is caused to develop from the reaction medium;

(b) performing a phosphonomethylation reaction in the solution obtained in step (a) in the presence of iminodiacetic acid in a molar ratio of iminodiacetic acid to phosphoric acid of between 1:1 and 1:1.2, with the addition of formaldehyde; and (c) recovering N-phosphono-methyl-imino-diacetic acid from the reaction medium.

DETAILED DESCRIPTION OF THE INVENTION

In the preferred embodiment of the process according to the invention, the hydrolysis of phosphorous trichloride is performed in step (a) using concentrated hydrochloric acid having a concentration of 30–38% so as to obtain an aqueous solution having a hydrochloric acid/phosphoric acid molar ratio of between 0.7:1 and 1.5:1, preferably between 0.9:1 and 1.1:1, at a hydrolysis temperature of between 30° C. and 70° C., and preferably between 40° C. and 50° C. As hydrolysis is performed in concentrated hydrochloric acid, the reaction is almost heatless and the chloride ions present from the beginning of the reaction, among other things, prevent the oxidation of the phosphoric acid.

Further advantages and features of the process according to the invention are evident from the following detailed description provided with references to FIGS. 1 and 2. The figures and detailed description are not meant to limit the scope of the invention.

Figure 1:
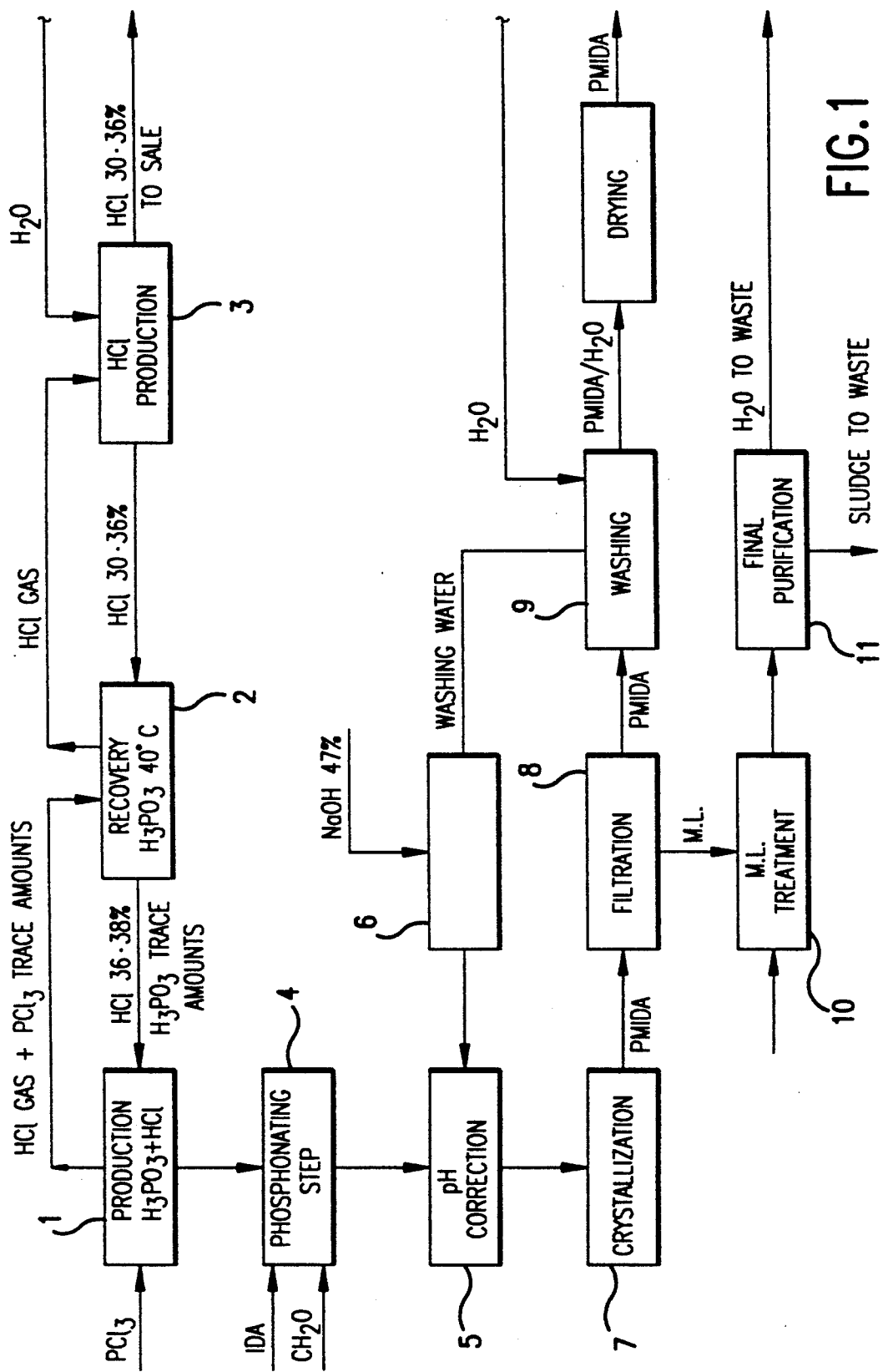
FIG. 1 is a flow chart of the process for producing PMIDA using IDA.

In FIG. 1, reference numeral 1 indicates a phosphorous trichloride hydrolysis stage (stage 1) in which the trichloride is hydrolysed by adding an aqueous solution of concentrated hydrochloric acid, having a concentration of 30–38% by weight, and preferably a concentration of 36–38% by weight, obtained from a phosphoric acid recovery stage, indicated by reference numeral 2 (stage 2). The hydrolysis reaction is performed in such a way that gaseous hydrochloric acid, possibly including traces of phosphorous trichloride, develops to obtain a solution of hydrochloric acid and phosphoric acid in which the molar ratio of the two acids is within the limits stated above.

The flow of gaseous hydrochloric acid along with possible traces of phosphorous trichloride passes to stage 2 for the recovery of the phosphoric acid, which is performed by absorption in concentrated hydrochloric acid at a temperature which is typically not greater than 40° C. From stage 2, the gaseous effluent consisting of hydrochloric acid is fed to stage 3 for the production of hydrochloric acid, advantageously producing a concentrated hydrochloric acid solution having a concentration which can be adjusted as desired from 30% to 36% by weight. The hydrochloric acid solution thereafter can be put to direct commercial use since it is not contaminated with undesirable impurities.

The solution of phosphoric acid and hydrochloric acid, present in the above molar ratios, is used in the phosphonomethylation stage, indicated by reference numeral 4 (stage 4) in FIG. 1, in which phosphonation is performed by adding IDA and formaldehyde at a temperature which is typically between 90° C. and 120° C. As is known, in order to improve the output, the phosphonomethylation reaction is preferably performed using a slight stoichiometric excess of formaldehyde and phosphoric acid relative to the molar concentration of IDA. Therefore, in general, when 1 mole of IDA is used in the phosphonation stage 4, between 1 and 1.2 moles of phosphorous trichloride are used for the hydrolysis of phosphorous trichloride in stage 1. The formaldehyde is preferably used in a stoichiometric excess of between 1 and 1.2, preferably 1.15, moles of formaldehyde per mole of IDA.

The iminodiacetic acid used in the phosphonomethylation stage can be prepared by known methods, as is described, for example, in British is Patent No. GB 1,575,569, by basic hydrolysis of iminodiacetonitrile (IDAN), followed by acidification of the hydrolysis product with strong mineral acid and crystallization of the IDA which is thereafter recovered by filtration.

In order to recover the required PMIDA compound from the phosphonomethylation medium, a pH correction operation is performed, indicated as stage 5 in FIG. 1, by adding to the reaction medium dilute sodium hydroxide, obtained, for example, from stage 6 at which the sodium hydroxide, typically concentrated to 47% by weight concentration, is diluted with the washing waters obtained from the crystallized product. The diluted sodium hydroxide is used in an amount such that the pH of the reaction medium is adjusted to about pH 2, and more precisely to near the isoelectric point of minimum solubility of the N-phosphono-methyliminodiacetic acid. Enough sodium hydroxide is used such that the hydrochloric acid present in the reaction mixture is completely neutralized. The hydrochloric acid is unable to be distilled since it generally forms an azeotrope with the water, and when concentrated, forms salts with the PMIDA itself. The process according to the invention allows the amount of sodium hydroxide solution to be reduced to a minimum. In addition, the losses of PMIDA in the mother liquor (abbreviated as "M.L." in FIGS. 1 and 2) are minimal.

When the pH has been corrected, the desired product crystallizes during a crystallization stage 7 at a temperature between 8° C. and 30° C. The crystallization product is then filtered in stage 8 and washed in stage 9.

The mother liquors obtained from filtration are subjected to a purification treatment identified as stages 10 and 11.

Figure 2:
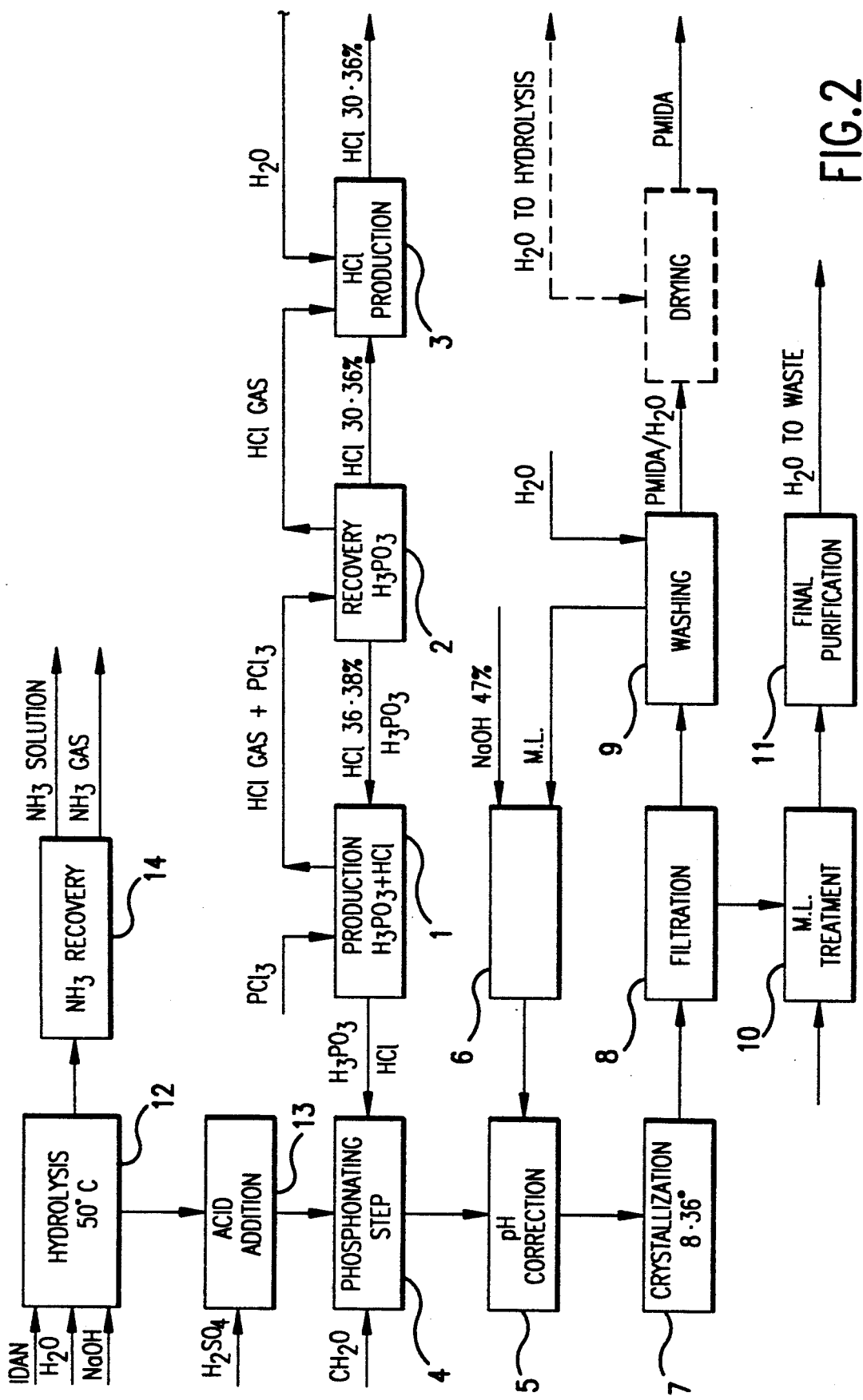
FIG. 2 is a flow chart of the process according to the invention for producing PMIDA from iminodiacetonitrile (IDAN).

In the flow chart of FIG. 2, operations similar to those described above with reference to FIG. 1 are indicated in FIG. 2 by the same reference numerals. The process diagram in FIG. 2 differs from that in FIG. 1 by the use of iminodiacetonitrile (IDAN) as the IDA source. As identified by stage 12 in FIG. 2, IDAN is subjected to basic hydrolysis with an aqueous solution having an alkaline base, particularly sodium hydroxide, at a temperature generally between 25° C. and 50° C. in order to form the alkali metal salt, particularly the sodium salt, of IDA. When the IDAN is hydrolysed, ammonia develops and is recovered at an absorption stage 14 with the production of an aqueous ammonia solution and/or gaseous ammonia. A strong mineral acid is added in stage 13 to the IDAN hydrolysis product in order to form the strong acid salt of IDA. The acidification product is then subjected to phosphonomethylation using the phosphoric acid and hydrochloric acid solution prepared in stage 1, as described above. In this variation of the process, the strong mineral acid used in the acidification stage 13 advantageously consists of sulfuric acid, as a result of which, the reaction mixture added to the product of hydrolysis of the phosphorous trichloride prepared in stage 1 comprises sodium sulfate.

The process according to the invention, as described above, comprises substantial advantages, for example:

it simplifies isolation of the products;

it saves energy, for among other reasons, as a result of eliminating the concentration of the reaction mass;

it increases the specific productivity of the equipment in terms of quantities produced with respect to the reaction volume used;

it uses scarcely one third of the hydrochloric acid generated by the phosphorous trichloride, and with the remaining two thirds, produces an industrial standard hydrochloric acid;

it significantly reduces the amount of refluents and their solubility and hence also reduces the relative disposal costs in terms of apparatus and treatment;

it reduces the loss of product which is due to its solubility in water;

it reduces the overall consumption of reagents.

It is understood that, although the process according to the invention has been described with reference to operations performed in stages, the process could also be performed discontinuously or continuously according to the procedures known to persons skilled in the art.

Example 1

A 250 ml flask provided with agitators, a thermometer, a charging funnel and refrigerant which drips down is immersed in a thermostatic bath.

The flask is charged with a solution from a first absorber. The solution is obtained from a prior test of 230 g, which when analyzed proved to contain 1.3% $H_3PO_3$ and 37% HCl.

The solution is heated to 40° C., and within approximately 2 hours, 151.5 g of phosphorous trichloride are added. The gases which develop are absorbed in an absorber (first absorber) also maintained at 40° C. and containing 210 g of HCl having a concentration of 32.3%. Finally, the gases which develop from the first absorber are absorbed in 290 g of water while the temperature is maintained at 20° C., producing a 32.4% hydrochloric acid solution of high purity, uncontaminated with phosphoric acid.

When $PCl_3$ has been added, the flask weighs 221 g and contains 40.8% $H_3PO_3$ and 22.2% HCl. This liquid is transferred to a flask, approximately 750 ml in size which is provided with agitators, a thermometer and a charging funnel. 133.5 g iminodiacetic acid are added to the flask, and the mixture is heated to 90° C. When this temperature has been reached, 75 g of a 45% by weight formaldehyde solution are added within 60 minutes. After the formaldehyde solution has been added, the mixture is refluxed for 3 hours.

The mixture is then cooled to 40° C. 260 g of a 20% sodium hydroxide solution obtained from the reaction of 47% sodium hydroxide and the washing waters from a previous operation are added.

The mixture is agitated at 50° C. until a stable pH is attained and then is cooled to ambient temperature and left to crystallize. Filtration is then performed. The filtration liquors are then passed to a processing reactor which renders the liquors suitable for discharge. The product left behind on the filter is washed with water, whereafter the washing water is preserved for use in the dilution of the caustic soda for a later test. The product on the filter is dried, producing 210 g of phosphonomethyliminodiacetic acid having 97% purity.

What is claimed is:

1. A process for preparing N-phosphono-methyliminodiacetic acid by means of phosphonomethylation of iminodiacetic acid by the reaction of an aqueous solution of phosphoric acid and hydrochloric acid, obtained from the hydrolysis of phosphorous trichloride, with iminodiacetic acid and formaldehyde, comprising the steps of:

(a) hydrolysing the phosphorous trichloride with water or an aqueous solution of hydrochloric acid, the reaction temperature and amount of water are regulated such that an aqueous solution of hydrochloric acid and phosphoric acid in a molar ratio of 0.5:1 to 2:1 is formed, and gaseous hydrochloric acid is caused to is develop from the reaction medium;

(b) performing the phosphonomethylation reaction in the solution obtained in step (a) in the presence of iminodiacetic acid in a molar ratio of iminodiacetic acid to phosphoric acid of between 1:1 and 1:1.2, with the addition of formaldehyde; and (c) recovering N-phosphono-methyl-imino-diacetic acid from the reaction medium.

2. A process according to claim 1, wherein the iminodiacetic acid used in the phosphonomethylation reaction of step (b) is obtained by the basic hydrolysis of iminodiacetonitrile with an aqueous solution of sodium hydroxide and acidification with sulfuric acid in order to obtain sodium sulphate and iminodiacetic acid, wherein the reaction product is used as a source of iminodiacetic acid in the phosphonomethylation reaction of step (b).

3. A process according to claim 1, wherein an aqueous solution is obtained in step (a) having a hydrochloric acid/phosphoric acid molar ratio of between 0.7:1 and 1.5:1 and a hydrolysis temperature between 30° C. and 70° C.

4. A process according to claim 1, wherein the N-phosphono-methyl-imino-diacetic acid is recovered by adding to the phosphonomethylation product obtained in step (b) an aqueous solution of caustic soda and water for washing the product in order to cause the crystallization of the N-phosphono-methyl-iminodiacetic acid.

5. A process according to claim 1, wherein the gaseous hydrochloric acid developed in step (a) is absorbed in concentrated hydrochloric acid.

6. A process according to claim 1, wherein step (a) is performed by adding hydrochloric acid concentrated to between 30% and 38% by weight.

7. A process according to claim 3, wherein an aqueous solution is obtained in step (a) having a hydrochloric acid/phosphoric acid molar ratio between 0.9:1 and 1.1:1 and a hydrolysis temperature between 40° C. and 50° C.

* * * * *

UNITED STATES PATENT AND TRADEMARK OFFICE
CERTIFICATE OF CORRECTION

PATENT NO. : 5,312,973
DATED : May 17, 1994
INVENTOR(S) : G. Donadello

It is certified that error appears in the above-indentified patent and that said Letters Patent is hereby corrected as shown below:

In the abstract, line 8, "or" (second occurrence) should be --of--.

Col. 3, line 8, delete "is".

Signed and Sealed this

Sixteenth Day of August, 1994

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,312,973
DATED : May 17, 1994
INVENTOR(S) : Graziello Donadello

It is certified that error appears in the above-indentified patent and that said Letters Patent is hereby corrected as shown below:

Column 1, lines 18, 25, 32, 42, and 63, "phosphoric" should be
—phosphorous—.
lines 28, 29, 36, 37, 38, and 59, "phosphorous" should be —phosphorus—.
line 57, "N-phosphono-methyl-imini-diacetric" should be
—N-phosphono-methyl-imino-diacetic—.
Column 2, lines 1, 13, 20, 36-37, 41, 46, 57, and 66, "phosphoric"
should be —phosphorous—.
lines 9, 31-32, 40, and 45, "phosphorous" should be —phosphorus—.
Column 3, line 59, "phosphoric" should be —phosphorous—.
lines 1, 2, and 65, "phosphorous" should be —phosphorus—.
Column 4, line 41, "phosphoric" should be —phosphorous—.
Column 4, lines 8 and 33, "phosphorous" should be —phosphorus—.
Column 5, lines 2, 10, and 17, "phosphoric" should be —phosphorous—.
lines 3, and 6, "phosphorous" should be —phosphorus—.
Column 6, lines 6 and 23, "phosphoric" should be —phosphorous—.
Abstract, lines 4, 11, and 16, "phosphoric" should be —phosphorous—.
lines 5, and 6-7, "phosphorous" should be —phosphorus—.

Signed and Sealed this

Second Day of May, 1995

Attest:

BRUCE LEHMAN

*Attesting Officer*     *Commissioner of Patents and Trademarks*